Feb. 15, 1944. R. L. BYRUM Plant Pat. 616
ROSE PLANT
Filed Oct. 4, 1943
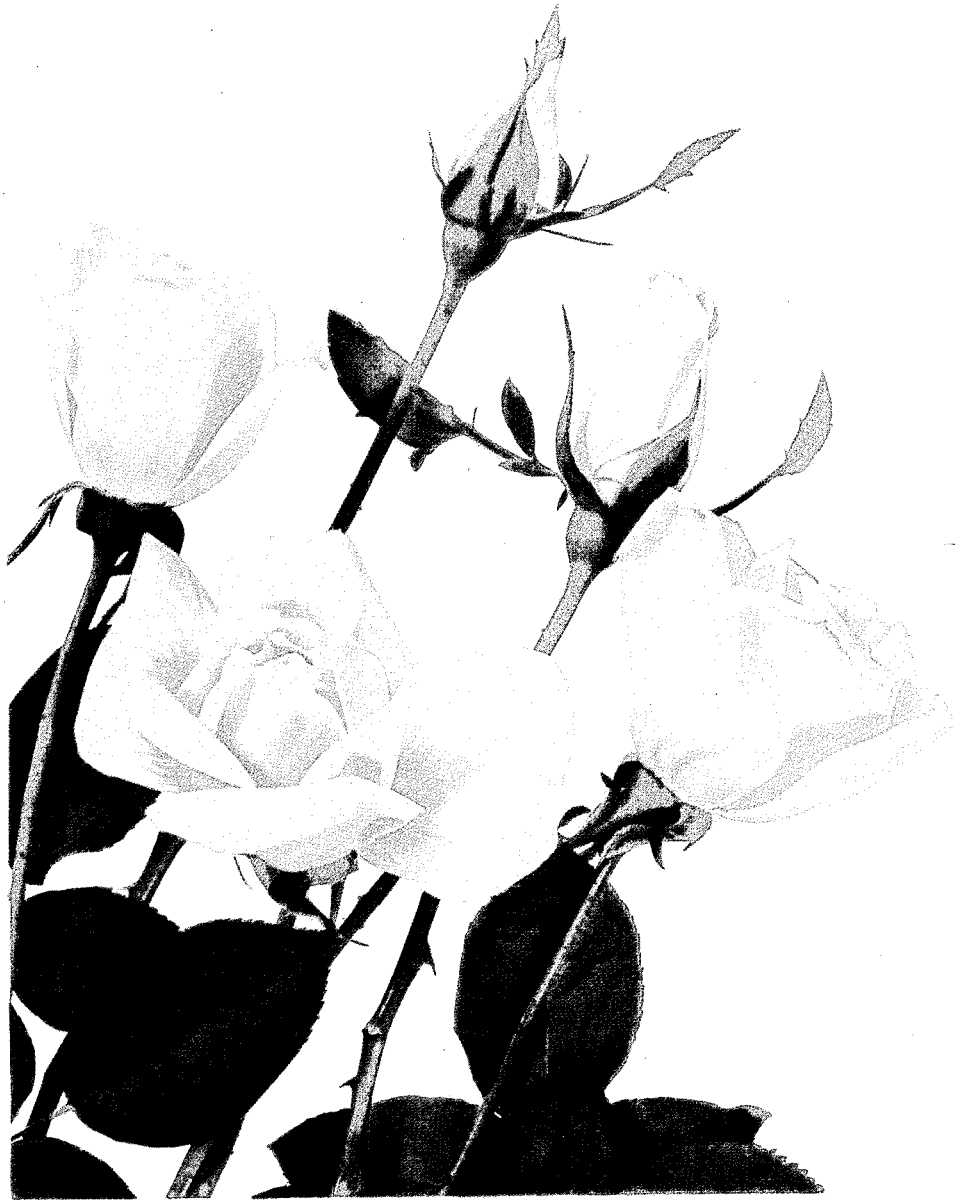
Inventor
Roy L. Byrum
By Robb & Robb
Attorneys Patented Feb. 15, 1944

UNITED STATES PATENT OFFICE

616

ROSE PLANT

Roy L. Byrum, Richmond, Ind., assignor to Joseph H. Hill Company, Richmond, Ind., a corporation of Indiana Application October 4, 1943, Serial No. 504,937

1 Claim. (Cl. 47—61)

The present invention relates to a new and distinct variety of rose plant, originated by crossing the two known varieties "Joanna Hill" and "California" (Pl. Pat. #449).

This new variety possesses many points of distinctiveness among roses of its type, primarily differing therefrom in point of color of the bloom, inasmuch as there appears to be nothing in greenhouse forcing varieties known by me which approaches it in color. Perhaps the nearest variety for comparison purposes is its pollen parent "California," but with respect to the latter, the blooms of the new variety have more petals, are better shaped, and open up more slowly. It does have growing habits somewhat similar to "California," but they differ materially from other greenhouse forcing varieties and will therefore bring new blood into the latter.

Asexual reproduction of this new variety shows the foregoing characteristics come true to form and are established.

The novel characteristics above referred to will become more apparent in the following detail description of the present rose, wherein color terminology accords with that of Ridgway's Color Standard, as and where designated; otherwise with usual dictionary significance:

Type: Tall; greenhouse; seedling: not tested outdoors.

Class: Hybrid tea.

Breeding: Seedling.

*Seed parent.*—"Joanna Hill."

*Pollen parent.*—"California."

Propagation: Holds its distinguishing characteristics through succeeding propagations by cuttings, grafting, and budding; layering not yet tried.

*Flower*

Locality where grown: Richmond, Indiana.

Flowers borne: Singly to stem; irregular; on strong, long stems.

Quantity of bloom: Abundant in greenhouse.

Continuity: Continuous.

Fragrance: Slight; tea.

Bud:

*Peduncle.*—Medium length; meduim heavy; erect; light green; almost smooth; numerous red hairs and prickles.

*Before calyx breaks.* — *Size* — Medium. *Form*—long, pointed, with a conspicuous neck; with foliaceous appendages on the surface of the bud; with stout, much cut foliaceous parts extending beyond the tip of the bud equal to three-fourths or more of its length.

*As calyx breaks.*—*Color*—Begonia Rose, Plate I.

*As first petal opens.*—*Size*—medium large. *Form* — long; pointed. *Color* — outside: base, Pale Lemon Yellow; Plate IV, shading to Begonia Rose, Plate I; inside: Lemon Yellow, Plate IV, shading through Strawberry Pink, Plate I, to Geranium Pink, Plate I. *Opening*—opens up well.

Bloom:

*Size.*—When fully open, medium large; 3½ to 4 inches. *Petalage.*—Double; from 30 to 40 petals arranged irregularly.

*Form.*—Full; high center at first; becoming open; petals remaining at first loosely rolled outward; becoming later, at maturity, very loosely rolled outward.

Petals: Thick; inside and outside shiny.

*Shape.*—Outside—obovate; apex flat. Intermediate—obovate with apex flat. Inside—lanceolate; scalloped irregular with one notch.

This description of a newly opened flower was made from a rose grown in a greenhouse during the month of March, 1942, at Richmond Indiana:

*Color.*—*Outside petal*—outside surface: base, Pale Lemon Yellow, Plate IV, shading to Jasper Pink, Plate XIII; inside surface: base, Lemon Yellow, Plate IV, shading to Venetian Pink, Plate XIII. *Intermediate petal*—outside surface; base, Pale Lemon Yellow, Plate IV, shading to Alizarene Pink, Plate XIII; inside surface: base, Lemon Yellow, Plate IV, shading to Jasper Pink, Plate XIII. *Inner petal*—outside surface: base, Pale Lemon Yellow, Plate IV, shading to Alizarene Pink, Plate XIII; inside surface: base, Lemon Yellow, Plate IV, shading to Jasper Pink, Plate XIII.

This description was made from a rose that was open for three days in a greenhouse in the month of April, 1942, at Richmond, Indiana:

*Color.*—*Outside petal*—outside surface: base, Pale Lemon Yellow, Plate IV, shading to Hermosa Pink, Plate I; inside surface: base, Lemon Yellow, Plate IV, shading to La France Pink, Plate I. *Intermediate petal*—outside surface: base, Pale Lemon Yellow, Plate IV, shading to La France Pink, Plate I; inner surface: base, Lemon Yellow, Plate IV, shading to Shrimp Pink, Plate I.

*General color effect.*—Newly opened flower—Jasper Pink, Plate XIII. Three days open—Hermosa Pink, Plate I.

*Behavior.*—Persist.

*Flower longevity.*—Cut roses grown in greenhouse kept at living-room temperatures—four to five days in April.

*Reproductive organs*

Stamens: Many; arranged irregularly about pistils; mixed with petaloids.
Filaments: Medium length, Yellow; most with anthers.
Anthers: Medium size; Yellow; all open at once.
Pollen: Moderate; Gold.
Pistils: Medium number.
Styles: Uneven; very short; medium heavy; bunched.
Stigma: Yellow.
Ovaries: All enclosed in calyx.
Sepals: Permanent; very long; spear-shaped; curled.
*Color.*—Inside—Light Bice Green, Plate XVII, with white fuzz over top. Outside—Light Bice Green, Plate XVII.

*Plant*

Foliage:
*Leaves.*—Compound of five to seven leaflets; abundant; medium large; leathery; wrinkled.
*Leaflets.*—*Shape*—ovoid; with apex acute; base round; margin, simply serrate.
*Color.*—*Mature*—upper surface: Moderately Dark Green; under surface: Light Green. *Young*—upper surface: Green-bronze; under surface: Light Bronze-red.
*Rachis.* — Heavy. Upper side — grooved; hairy; under side—moderately prickly.
*Stipules.* — Moderately short; moderately wide; with medium long points turning out at an angle of less than 45°.
*Disease.*—Resistant to mildew and blackspot insofar as this is evidenced by absence of any throughout development and establishing of this variety.

Growth:
*Habit.*—Bush; upright; much branched.
*Growth.*—Free; vigorous.
*Canes.*—Medium heavy.
*Main stems.*—Dull Green Bronze. *Thorns*—many; long; hooked downward; with long, narrow base. *Prickles*—several; Bronze red. *Hairs*—many; Red.
*Branches.*—Dull Green Bronze. *Thorns*—many; long; hooked downward; with long, narrow base. *Prickles*—several; reddish. *Hairs*—many; reddish.
*New shoots.*—Bronze Red. *Thorns*—many; medium long; hooked downward; with short, round base. *Prickles*—many; reddish. *Hairs*—many; reddish.

I claim:

A new and distinct variety of rose plant of the hybrid tea class, characterized as to novelty by its growing habits when compared with other greenhouse forcing varieties, the novel color of its blooms, number of petals, shape of the flower, and slow habit of opening of the same, substantially as shown and described.

ROY L. BYRUM.